(12) United States Patent
Schwartz et al.

(10) Patent No.: US 6,814,733 B2
(45) Date of Patent: Nov. 9, 2004

(54) RADIO FREQUENCY PULMONARY VEIN ISOLATION

(75) Inventors: Yitzhack Schwartz, Haifa (IL); Assaf Govari, Haifa (IL); Uri Yaron, Zichron-Yaacov (IL); Marcia Leatham, Orange, CA (US); Michael Levin, Haifa (IL)

(73) Assignee: Biosense, Inc., New Brunswick, NJ (US)

(*) Notice: Subject to any disclaimer, the term of this patent is extended or adjusted under 35 U.S.C. 154(b) by 111 days.

(21) Appl. No.: 10/062,698

(22) Filed: Jan. 31, 2002

(65) Prior Publication Data

US 2003/0144658 A1 Jul. 31, 2003

(51) Int. Cl.[7] .............................................. A61B 18/18
(52) U.S. Cl. ............................ 606/41; 606/45; 607/88; 607/112; 607/113; 607/116; 128/898
(58) Field of Search ................................ 606/7, 13–16, 606/41, 45, 46, 187; 607/88, 92, 116, 112, 113; 128/898

(56) References Cited

U.S. PATENT DOCUMENTS

| | | | |
|---|---|---|---|
| 4,979,948 A | 12/1990 | Geddes et al. | |
| 5,366,490 A | 11/1994 | Edwards et al. | |
| 5,391,199 A | 2/1995 | Ben-Haim | |
| 5,433,708 A | 7/1995 | Nichols et al. | |
| 5,807,395 A | 9/1998 | Mulier et al. | |
| 5,840,025 A | 11/1998 | Ben-Haim | |
| 5,891,134 A | 4/1999 | Goble et al. | |
| 5,938,600 A | 8/1999 | Van Vaals et al. | |
| 5,971,983 A | 10/1999 | Lesh | |
| 6,004,269 A | 12/1999 | Crowley et al. | |
| 6,012,457 A | 1/2000 | Lesh | |
| 6,024,740 A | 2/2000 | Lesh et al. | |
| 6,064,902 A | 5/2000 | Haissaguerre et al. | |
| 6,090,084 A | 7/2000 | Hassett et al. | |
| 6,117,101 A | 9/2000 | Diederich et al. | |
| 6,164,283 A | 12/2000 | Lesh | |
| 6,190,382 B1 | 2/2001 | Ormsby et al. | |
| 6,245,064 B1 | 6/2001 | Lesh et al. | |
| 6,251,109 B1 | 6/2001 | Hassett et al. | |
| 6,632,223 B1 * | 10/2003 | Keane ........................ 606/41 |
| 2002/0004644 A1 | 1/2002 | Koblish | |
| 2003/0125726 A1 | 7/2003 | Maguire et al. | |

FOREIGN PATENT DOCUMENTS

| | | |
|---|---|---|
| EP | 1042990 A | 10/2000 |
| WO | WO 00 66016 A | 11/2000 |
| WO | WO 01 19269 A | 3/2001 |

OTHER PUBLICATIONS

European Search Report, EP 03 25 0562, May 2, 2003.
Eigler NL et al., "Implantation and Recovery of Temporary Metallic Stents in Canine Coronary Arteries", J Am Coll Cardiol 1993;22(4)1207–1213.
Ware D et al., "Slow Intramural Heating with Diffused Laser Light: A Unique Method for Deep Myocardial Coagulation", Circulation; Mar. 30, 1999(12);1630–1636.
Wang PJ et al., "Alternate Energy sources for Catheter Ablation", Curr Cardiol Rep Jul. 1999;1(2):165–171.

(List continued on next page.)

Primary Examiner—Rosiland Rollins
(74) Attorney, Agent, or Firm—Louis J. Capazzuto

(57) ABSTRACT

A catheter introduction apparatus provides a radially expandable helical coil as a radiofrequency emitter. In one application the emitter is introduced percutaneously, and transseptally advanced to the ostium of a pulmonary vein. The emitter is radially expanded, which can be accomplished by inflating an anchoring balloon about which the emitter is wrapped, in order to cause the emitter to make circumferential contact with the inner wall of the pulmonary vein. The coil is energized by a radiofrequency generator, and a circumferential ablation lesion is produced in the myocardial sleeve of the pulmonary vein, which effectively blocks electrical propagation between the pulmonary vein and the left atrium.

36 Claims, 5 Drawing Sheets

OTHER PUBLICATIONS

Keane D et al., "Linear Atrial Ablation with a Diode Laser and Fiber Optic Catheter", Circulation 1999;100;e59–e60.

Scheinman NM et al., "Nonpharmacological Approaches to Atrial Fibrillation", Circulation 2001;103:2120–2125.

Natale A et al., "First Human Experience With Pulmonary Vein Isolation Using a Through–the–Balloon Circumferential Ultrasound Ablation System for Recurrent Atrial Fibrillation", Circulation 102:1879–1882 (2000).

Pappone C et al., "Circumferential Radiofrequency Ablation of Pulmonary Vein Ostia: A New Anatomic Approach for Curing Atrial Fibrillation", Circulation 102:2619–2628 (2000).

Middleton JC et al., "Synthetic Biodegradable Polymers as Orthopedic Devices", Biomaterials 21 (2000) 2335–2346.

Fried NM et al., "Linear Lesions in Myocardium Created by Nd:YAG Laser Using Diffusing Optical Fibers: In vitro and In Vivo Results", Lasers Surg Med 2000;27:295–304.

* cited by examiner

FIG. 1B
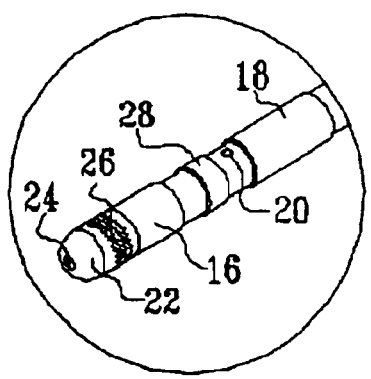
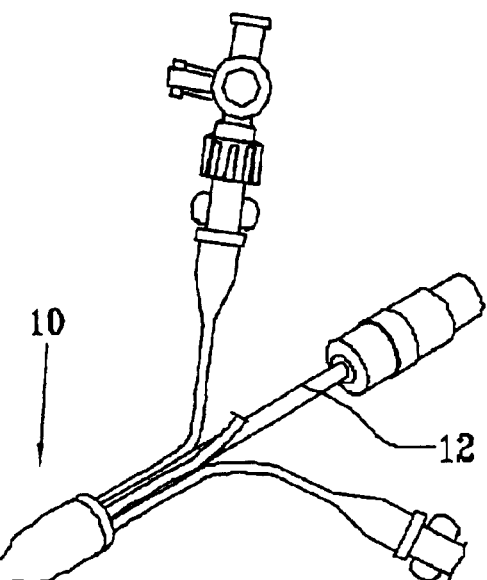
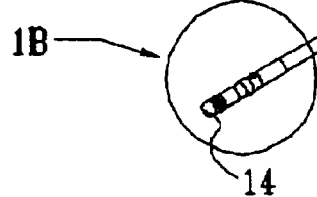
FIG. 1A
FIG. 2
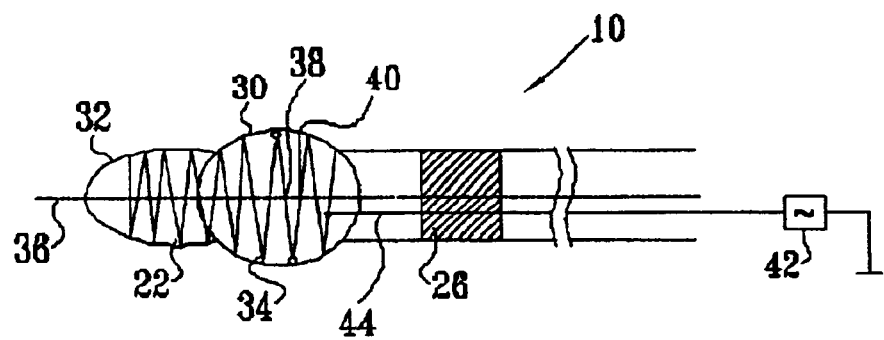

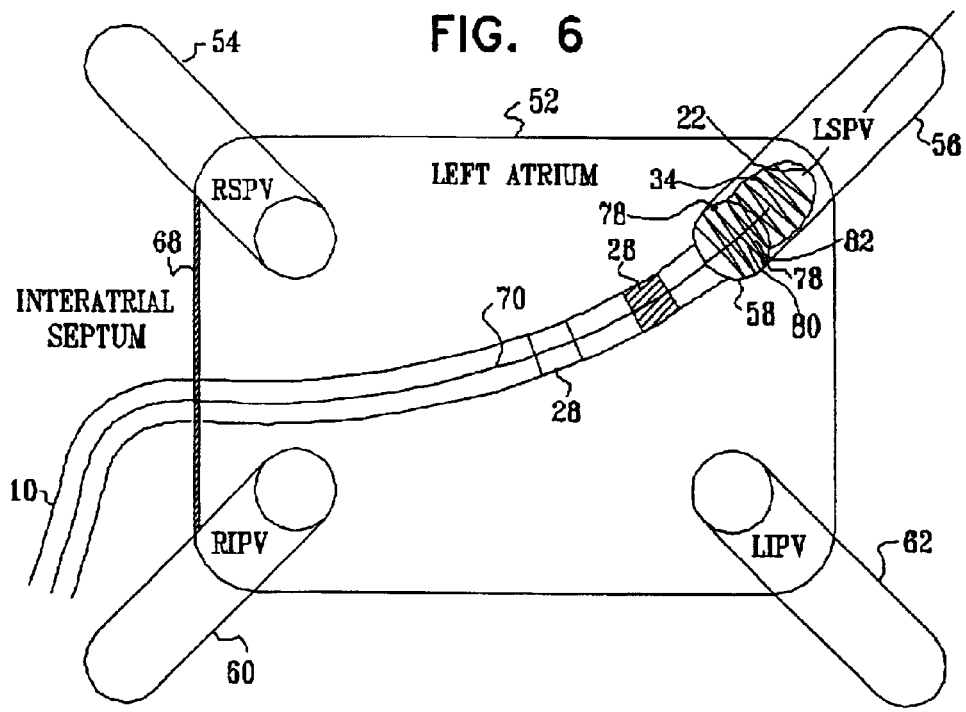
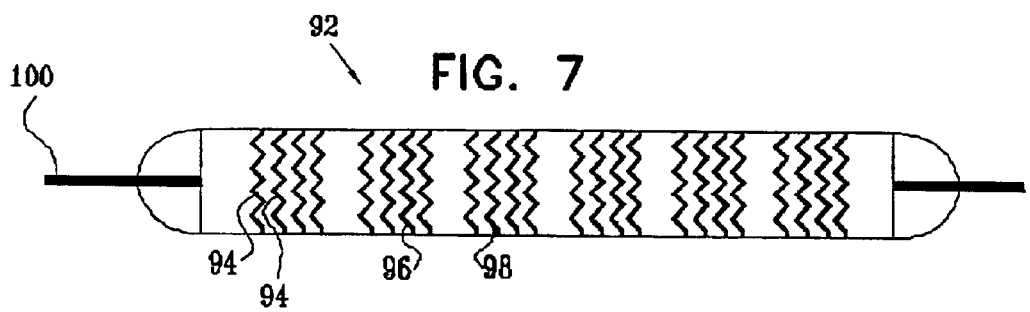
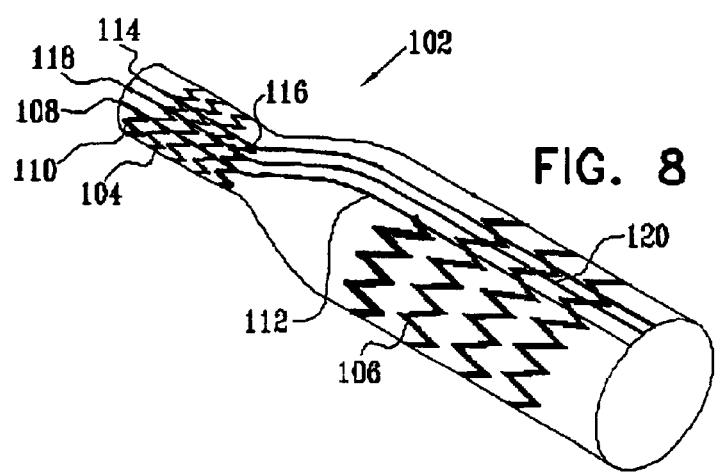

RADIO FREQUENCY PULMONARY VEIN ISOLATION

BACKGROUND OF THE INVENTION

1. Field of the Invention

This invention relates to methods and apparatus for the medical treatment of disease of the heart. More particularly, this invention relates to a method and apparatus for treating cardiac arrhythmias by ablating in a vicinity of pulmonary venous tissue.

2. Description of the Related Art

Tissue ablation from the inner walls of hollow viscera of the body generally, and the vascular system in particular, has been found to be useful in the treatment of various medical conditions. Technological developments in intravascular catheters, manipulative instruments adapted to intravascular catheters, and catheter localization techniques have especially benefited the field of cardiology. Percutaneous transcatheter ablation has been used successfully in the treatment of conduction defects and arrhythmias of various types. Today, atrial tachyarrhythmias are a common application for ablative therapy.

Various ablative modalities have been employed in the past, such as ablation by direct heating. Energy can be conducted to the target tissue using various modalities, such as ultrasound, laser, resistive heating, and radiofrequency energy.

One ablative approach is the so-called "maze" technique. In general, the maze procedure attempts to block abnormal conduction patterns in the left atrium by establishing a maze-like pattern of linear lesions in the left atrial wall.

Atrial arrhythmias are known to be associated with abnormal electrical activity of tissue foci in the vicinity of the pulmonary veins, especially the superior pulmonary veins. Various ablative treatments of such foci have been attempted. For example, the production of linear atrial lesions by radiofrequency ablation, in combination with ablation of suspected arrhythmogenic foci has been performed using transcatheter techniques.

More recently, circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

Radiofrequency ablation using multiple contiguous circumferential points, guided by electro-anatomical mapping is proposed in the document, *Circumferential Radiofrequency Ablation of Pulmonary Vein Ostia: A New Anatomic Approach for Curing Atrial Fibrillation*, Pappone C, Rosanio S, Oreto G, Tocchi M, Gugliotta F, Vicedomini G, Salvati A, Dicandia C, Mazzone P, Santinelli V, Gulletta S, Chierchia S, Circulation 102:2619–2628 (2000). It is emphasized that particular care must be exercised to ensure that the ablation sites are indeed contiguous; otherwise irregular electrical activity in the pulmonary vein may continue to contribute to atrial arrhythmia.

It has also been proposed to produce circumferential ablative lesions using ultrasound delivered through a balloon. This technique is described, for example, in the document, *First Human Experience With Pulmonary Vein Isolation Using a Through-the-Balloon Circumferential Ultrasound Ablation System for Recurrent Atrial Fibrillation*, Natale A, Pisano E, Shewchik J, Bash D, Fanelli R, MD; Potenza D; Santarelli P; Schweikert R; White R; Saliba W; Kanagaratnam L; Tchou P; Lesh M, Circulation 102:1879–1882 (2000).

A known drawback in the use of radiofrequency energy for cardiac tissue ablation is the difficulty in controlling the local heating of tissue. There are tradeoffs between the clinical desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

In consideration of these, and other factors, it is appropriate, in designing a practical radiofrequency electrode, to consider the amplitude of the radiofrequency signal, the amount of time required for the energy application, the size of the electrode, and the contact area, as well as ease of positioning, withdrawal, and repositioning of the device so as to be able to conveniently produce multiple lesions during the same medical procedure.

Previous approaches to controlling local heating include the inclusion of thermocouples within the electrode and feedback control, modulation of the radiofrequency signal, local cooling of the catheter tip, and fluid assisted techniques, for example perfusion of the target tissue during the energy application, using chilled fluids. Typical of the last approach is Mulier, et al. U.S. Pat. No. 5,807,395.

Known solutions to electrical pulmonary vein isolation typically require four to seven radiofrequency applications for completion of the isolation of each pulmonary vein. Other techniques utilize a coil within an expandable balloon. Radiofrequency or ultrasound energy from the coil is passed through the balloon together with a conductive fluid, into surrounding tissue.

Publications which describe various medical techniques of interest include:

1. Scheinman M M, Morady F. Nonpharmacological Approaches to Atrial Fibrillation. *Circulation* 2001; 103:2120–2125.
2. Wang P J, Homoud M K, Link M S, Estes III N A. Alternate energy sources for catheter ablation. *Curr Cardiol Rep* 1999 July; 1(2):165–171.
3. Fried N M, Lardo A C, Berger R D, Calkins H, Halperin H R. Linear lesions in myocardium created by Nd:YAG laser using diffusing optical fibers: in vitro and in vivo results. *Lasers Surg Med* 2000; 27(4):295–304.
4. Eigler N L, Khorsandi M J, Forrester J S, Fishbein M C, Litvack F. Implantation and recovery of temporary metallic stents in canine coronary arteries. *J Am Coll Cardiol* 1993; 22(4):1207–1213.
5. Synthetic Biodegradable Polymers as Medical Devices; by John C. Middleton and Arthur J. Tipton. 1998.
6. Keane D, Ruskin J, Linear atrial ablation with a diode laser and fiber optic catheter. *Circulation* 1999; 100:e59–e60.
7. Ware D, et al., Slow intramural heating with diffused laser light: A unique method for deep myocardial coagulation. *Circulation*; Mar. 30, 1999; pp. 1630–1636.

Other medical technologies of interest are described in U.S. Pat. No. 5,891,134 to Goble et al., U.S. Pat. No. 5,433,708 to Nichols et al., U.S. Pat. No. 4,979,948 to Geddes et al., U.S. Pat. No. 6,004,269 to Crowley et al., U.S. Pat. No. 5,366,490 to Edwards et al., U.S. Pat. Nos. 5,971,983, 6,164,283, and 6,245,064 to Lesh, U.S. Pat. No. 6,190,382 to Ormsby et al., U.S. Pat. Nos. 6,251,109 and 6,090,084 to Hassett et al., U.S. Pat. No. 5,938,600 to Swartz et al., U.S. Pat. No. 6,064,902 to Haissaguerre et al., and U.S. Pat. No. 6,117,101 to Diederich et al.

All of the patents and publications cited in this disclosure are incorporated herein by reference.

SUMMARY OF THE INVENTION

It is therefore a primary object of some aspects of the present invention to provide improved apparatus and methods for electrically isolating the pulmonary vein by accomplishing a circumferential conduction block surrounding the pulmonary vein ostium in a single ablation application.

It is another object of some aspects of the present invention to reduce the time required to perform electrical isolation of the pulmonary veins.

These and other objects of the present invention are attained by a medical device comprising a catheter introduction apparatus in combination with a radiofrequency emitter that comprises a radially expandable helical coil, which is fabricated from a shape memory alloy. The distal end of the catheter introduction apparatus is placed at a desired location at the ostium of a pulmonary vein. The coil is energized, and an ablation lesion is produced, preferably by the transfer of a single application of radiofrequency energy from the coil to tissue in the ostium of the pulmonary vein.

In one embodiment, the helical coil is expanded by joule heating from a radiofrequency generator to conform to the lumen of the pulmonary vein and to come into a circumferential contacting relationship therewith.

Alternatively or additionally, the helical coil is wrapped about a balloon and is expanded by inflation of the balloon until it is brought into a circumferential contacting relationship with the endothelial surface of the pulmonary vein.

In a further embodiment of the invention, the helical coil is constructed of a biodegradable material, and is left in place following the ablative procedure.

The invention provides a method for electrically isolating a cardiac chamber, including the steps of introducing a coil into a pulmonary vein proximate an ostium of the pulmonary vein, wherein a principal axis of the coil is substantially aligned coaxially with the pulmonary vein, circumferentially engaging the coil with an inner wall of the pulmonary vein to define a circumferential region of contact between the coil and the pulmonary vein, and while maintaining the circumferential region of contact, conducting radiofrequency energy from the coil to the circumferential region of contact to ablate tissue in an ablation region of the pulmonary vein.

In one aspect of the invention, the coil is constructed of a shape memory alloy. When the temperature of the alloy is varied, the coil radially expands to engage the inner wall of the pulmonary vein.

According to another aspect of the method, the when heated, coil becomes tapered, such that the proximal segment of the coil is more radially expanded than the distal segment thereof.

In a further aspect of the method the coil axially expands when heated.

In yet another aspect of the method the shape of the coil is adjusted by differentially heating segments of the coil. Differential heating can be achieved by passing different amounts of current through different ones of the segments of the coil, or by inductive heating.

In still another aspect of the method differential heating is achieved by subjecting the coil to a single electromagnetic influence for heating thereof, and conducting a coolant to selected segments of the coil.

According to still another aspect of the method, a width dimension of the ablation region is at least as large as the pitch of the coil.

An additional aspect of the method introducing includes transferring the coil into the heart through the interatrial septum, and while transferring the coil through the interatrial septum, conducting radiofrequency energy a second time from the coil into the interatrial septum to ablate tissue of the interatrial septum. Radiofrequency energy is conducted the second time until a sufficient amount of the tissue of the interatrial septum has been ablated to accommodate passage of the coil therethrough.

According to yet another aspect of the method, the coil is constructed of a biodegradable material.

In still another aspect of the method radiofrequency energy is conducted to the ablation region in a single continuous application.

In another aspect of the method the coil is circumferentially engaged by disposing the coil about an anchoring balloon, and inflating the anchoring balloon to radially expand the coil. The anchoring balloon can be bilobate or pyriform when expanded.

The method is applicable to hollow viscera other than the heart and the pulmonary veins.

BRIEF DESCRIPTION OF THE DRAWINGS

For a better understanding of these and other objects of the present invention, reference is made to the detailed description of the invention, by way of example, which is to be read in conjunction with the following drawings, wherein:

FIGS. 1A and 1B, collectively referred to herein as FIG. 1, illustrate a therapeutic catheter that is constructed and operative in accordance with a preferred embodiment of the invention;

FIG. 2 is an enlarged schematic illustration of the distal end of the catheter shown in FIG. 1 with an inflation balloon expanded, and a radiofrequency ablation element in place;

FIG. 6 schematically illustrates certain aspects of a method of intracardiac catheter access during a third phase of the method shown in FIG. 3;

FIG. 7 is a schematic view of a coil that is constructed and operable in accordance with an alternate embodiment of the invention;

FIG. 8 is a schematic view of a coil having a shape memory that is constructed and operative in accordance with an alternate embodiment of the invention shown following an application of heat;

DESCRIPTION OF THE PREFERRED EMBODIMENTS

Figure 3:
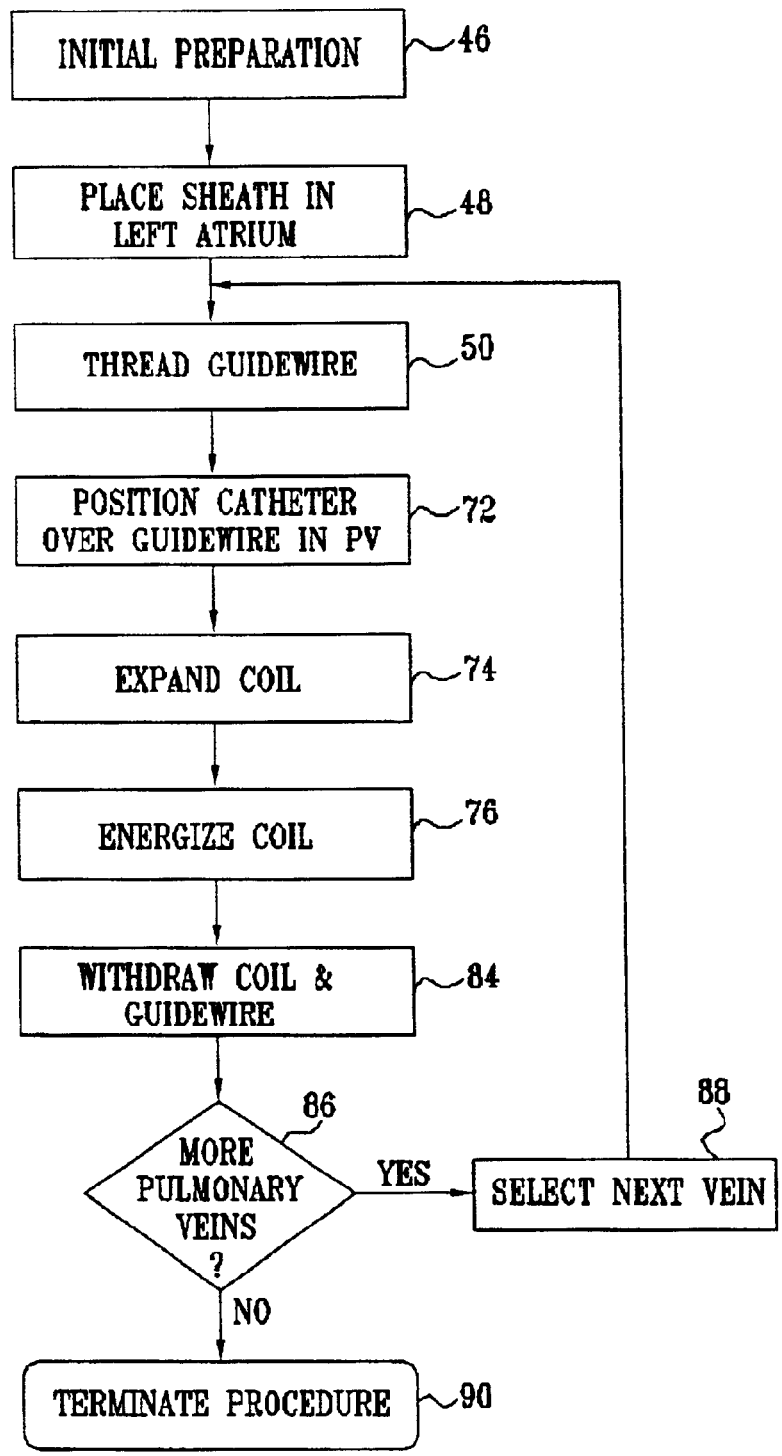
FIG. 3 is a flow chart of a method for electrically isolating the pulmonary vein, which is operative in accordance with a preferred embodiment of the invention.

In the following description, numerous specific details are set forth in order to provide a thorough understanding of the present invention. It will be apparent to one skilled in the art, however, that the present invention may be practiced without these specific details. In other instances, well known circuits, control logic, and other apparatus have not been shown in detail in order not to unnecessarily obscure the present invention. The embodiments are disclosed with reference to a particular anatomic site. However, the invention can be practiced in many anatomic sites where it is desirable to ablate tissue in the walls of hollow viscera.

Turning now to the drawings, reference is made to FIGS. 1A and 1B, which illustrate a medical device that is constructed and operative in accordance with a preferred embodiment of the invention. An intravascular catheter 10 has a proximal end 12 and a distal end 14. The distal end 14 is provided with at least one seal 16, and optionally a second seal 18. The seals 16, 18 are preferably inflatable balloons, made from rubber, polyurethane, or a similar elastic material. The catheter 10 has one or more lumens, which conduct fluid for inflating and deflating the seals 16, 18. One of the lumens terminates in a port 20, and is useful for injection of fluids and withdrawal of blood as may be required during use. Other lumens are provided for passage of guidewires and instruments therethrough. An inflatable anchoring balloon 22, shown in a deflated condition, is located distal to the seals 16, 18. The catheter 10 also has a coaxial guidewire lumen 24.

Preferably the active sites to be ablated are identified using the location and mapping system disclosed in commonly assigned U.S. Pat. No. 5,840,025 and U.S. Pat. No. 5,391,199 which are herein incorporated by reference. For the embodiment of U.S. Pat. No. 5,840,025, certain components of the location and mapping system are incorporated into the distal end 14 of the catheter 10, namely a mapping electrode 26 and a transmitting antenna 28, which can be a dipole antenna. The mapping electrode 26 detects local electrical activity of the heart, and the antenna 28 transmits signals to a plurality of receiving antennae (not shown) which are placed on the body surface of a patient during use. The distal end 14 can be radio-opaque, in order to facilitate its localization by conventional radiographic techniques, alternatively or in addition to the system disclosed in the above-noted U.S. Pat. No. 5,840,025.

For the embodiment disclosed in U.S. Pat. No. 5,391,199 certain components of the location and mapping system are incorporated into the distal end 14 of the catheter 10, namely the mapping electrode 26 and a location sensor 28, which is a position and orientation sensor. The mapping electrode 26 detects local electrical activity of the heart, and the location sensor 28 receives electromagnetic field signals from a plurality of electromagnetic field generators (not shown) which are placed exterior of the patient such as on the body surface of a patient during use and transmit electromagnetic fields to define a frame of reference in order to track the position and orientation of the catheter distal end 14. Thus, based on the electromagnetic fields received at the location sensor 28, the location sensor 28 transmits a location signal to the signal processor/control system (not shown) by providing at least 5 dimensions of position and orientation information (X, Y, Z, Pitch and Yaw) in the form of coordinate information and, in some embodiments provide 6 dimensions of position and orientation information (X, Y, Z, Pitch, Yaw and Roll) in the form of coordinate information. The distal end 14 can be radio-opaque, in order to facilitate its localization by conventional radiographic techniques, alternatively or in addition to the system disclosed in the above-noted U.S. Pat. No. 5,391,199.

In embodiments in which the system disclosed in the above-noted U.S. Pat. Nos. 5,840,025 and 5,391,199 is not used, the mapping electrode 26 performs conventional monitoring of local electrical activity, and the antenna 28 can be omitted.

Reference is now made to FIG. 2, which is a partially schematic enlarged view of the distal end 14 of the catheter 10 shown in FIG. 1. The anchoring balloon 22 is inflated, and preferably has a large-radius proximal lobe or segment 30, and a small-radius distal lobe or segment 32. The bilobate configuration of the anchoring balloon 22 aids in securely positioning it within the ostium of a pulmonary vein. Alternatively the anchoring balloon 22 can be pyriform, ellipsoidal, or otherwise constructed, so long as its proximal portion is more radially expanded than its distal portion e.g. the proximal portion has a larger expanded diameter than the expanded diameter of the distal portion. The anchoring balloon 22 is constructed of conventional materials. Securely wrapped about the external surface of the anchoring balloon 22 is a distally tapering helical coil 34 or stent, preferably constructed of nickel titanium (nitinol) or other shape memory alloy. This material is suitable for use within the body and can easily be heated up by applying voltage. It can be readily formed into a desired shape by well-known techniques. The axis of the coil 34 and the axis of the anchoring balloon 22 are both generally aligned, as indicated by a line 36. The pitch of the coil 34 is represented by the linear distance between the same points on adjacent loops, for example the distance between a point 38 and a point 40 on the line 36. The pitch of different segments of the coil 34 may vary.

The coil 34 is connected to a suitable radiofrequency generator 42 by a lead 44. The coil 34 is preferably formed of 0.1 mm. gauge wire and has about 4–5 turns, its preferred length is about 2–3 cm. The helix angle is not critical. In any case, a certain amount of deformation occurs during placement. The length of the expanded coil varies with the application.

The helical shape of the coil 34 has important advantages, compared with other known elements that have been used in the past for circumferential pulmonary vein isolation. In some applications, it may be desirable to allow the coil 34 to remain in situ following an ablative procedure, and because of its helical shape, the coil 34 is adaptable for use as a stent. Construction is simple, and the pitch and taper of the spiral can be readily adjusted for individual variations in the anatomy of the various pulmonary veins, either by selecting a coil from a series of coils having standard sizes, or through ad hoc modification by the operator. It is believed to be less expensive to reliably construct a simple spiral than the more complex structures that are disclosed, for example, in the above-noted U.S. Pat. No. 6,012,457. The helical shape takes full advantage of the shape memory properties of the alloy, which promotes ease of use, radial expansion and contraction, and withdrawal following completion of the ablative lesion.

More generally, use of the coil as described facilitates the creation of a complete line of block surrounding the pulmonary vein ostium in a single ablation application. By contrast, some currently available techniques require multiple RF ablations, e.g., four to seven ablations, for completion of the isolation of each pulmonary vein. Other techniques utilize a coil within an expandable balloon, whereby radiofrequency energy from the coil is passed to a conductive fluid in the balloon, then through the balloon, and only at that point into surrounding tissue. Advantageously, procedures performed using the coil provided by this embodiment of the present invention are believed to be simpler, quicker, and more efficient than those which use the methods provided by the prior art.

Preferably the coil 34 is securely attached to the anchoring balloon 22 or the distal end 14 of the catheter 10, and is removed from the pulmonary vein ostium when the catheter 10 is withdrawn at the completion of the procedure.

In some embodiments, the coil 34 is made of a biodegradable material, for example polymer polylactide and trimethylene carbonate polymers. In these embodiments, the coil 34 is expanded sufficiently prior to or during the ablation to become securely circumferentially attached to the wall of the pulmonary vein. It is detachable from the anchoring balloon 22 or the distal end 14 of the catheter 10. In these embodiments the coil 34 remains firmly engaged circumferentially with the inner lining of the pulmonary vein as a result of its elasticity and shape memory. The coil 34 is allowed to remain in situ following the ablation procedure, and it is eventually resorbed. In such embodiments, the continued stenting of the pulmonary vein by the coil may reduce the risk of contracture and stenosis of the pulmonary veins. Additionally, in some embodiments, the coil 34 (stent) is coated with a drug for preventing stenosis of the vessel. The coating on the coil 34 may be used to deliver therapeutic and pharmaceutic agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as $G(GP)II_bIII_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

Reference is now made to FIG. 3, which is a flow chart of a method for electrically isolating pulmonary veins, which is operative in accordance with a preferred embodiment of the invention. The description of FIG. 3 should be read in conjunction with FIGS. 1 and 2.

In initial step 46 routine preparation of a subject (not shown) and equipment are accomplished. This includes attachment of various monitoring and grounding leads, as may be required for electrophysiological monitoring of the procedure, and for the operation of the above-noted location and mapping system.

Next, at step 48, a series of events begins, ultimately leading to the positioning of the catheter 10 and the coil 34 at the ostium of a pulmonary vein. Step 48 is conventional. In a preferred approach, the venous system is accessed using the well-known Seldinger technique, in which an introducer sheath is positioned in a peripheral vein, typically a femoral vein. A guiding sheath is introduced through the introducer sheath, and is advanced via the inferior vena cava into the right atrium. Then, using a Brockenbrough needle, the fossa ovalis of the interatrial septum is punctured, and the puncture dilated if necessary. The Brockenbrough needle is withdrawn, and the guiding sheath placed in the left atrium. Alternatively, the ablation catheter is energized as it contacts the interatrial septum, usually at the fossa ovalis. Ablation of septal tissue eases the passage of the catheter through the septum, reduces the amount of hardware used, and shortens the procedure, as it is not necessary to pass a dilator through the fossa ovalis. It is also possible to access the left atrium via the superior vena cava, or to use a retrograde intraarterial technique.

Next, in step 50 a guidewire is advanced through the guiding sheath, through the left atrial chamber, into a pulmonary vein.

The order in which the specific pulmonary veins are visited and treated is arbitrary, but it is preferable to concentrate first on the two superior pulmonary veins, in which the muscular sleeves are more prominent than in the inferior pulmonary veins. Thereafter the inferior pulmonary veins may be isolated. Typically, an ablation procedure involves the isolation of all four pulmonary veins.

Figure 4:
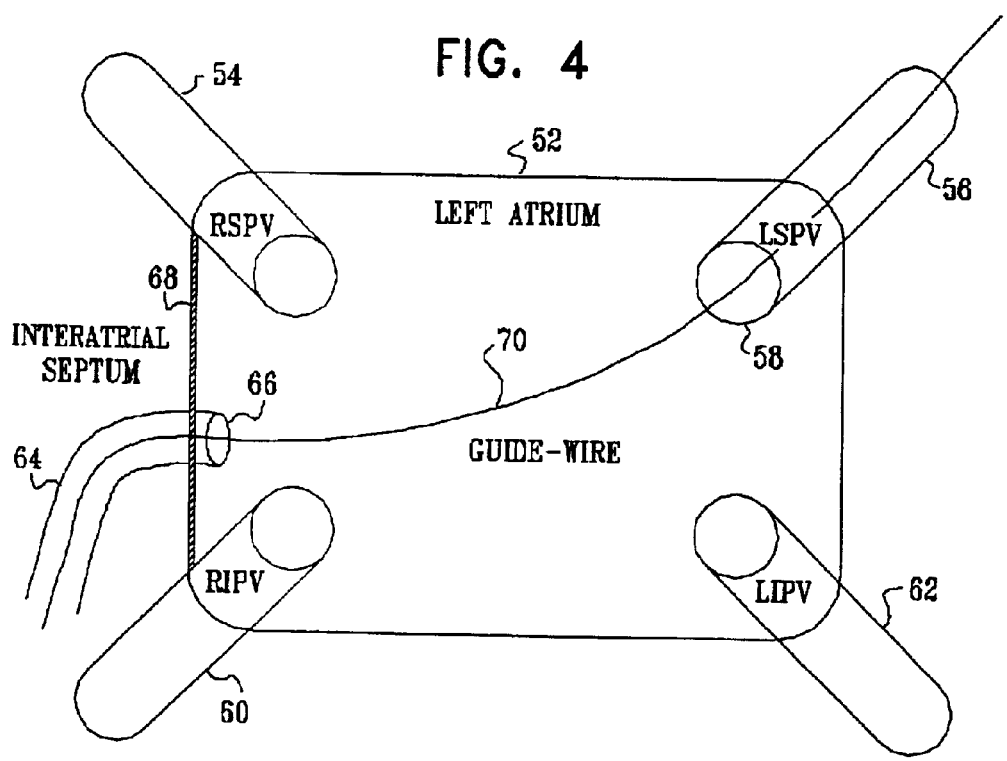
FIG. 4 schematically illustrates certain aspects of a method of intracardiac catheter access during a first phase of the method shown in FIG. 3.

Reference is now made to FIG. 4, which schematically illustrates certain aspects of the method of electrical pulmonary vein isolation in accordance with a preferred embodiment of the invention. The description of FIG. 4 should be read in conjunction with FIG. 3. FIG. 4 represents the status at the completion of step 50 (FIG. 3). A cutaway view of a left atrial chamber 52 includes a right superior pulmonary vein 54 and a left superior pulmonary vein 56, whose ostium 58 is indicated. The view of FIG. 4 also includes a right inferior pulmonary vein 60, and a left inferior pulmonary vein 62. A conventional guiding sheath 64 has a distal end 66, which has been positioned, on the left atrial side of an interatrial septum 68. A conventional guidewire 70 extends through the lumen of the guiding sheath 64, into the lumen of the left superior pulmonary vein 56. It will be understood that while the guidewire 70 is shown in relation to the left superior pulmonary vein 56, the technique is equally applicable to the other pulmonary veins.

Referring again to FIG. 3, at step 72, the guiding sheath is withdrawn, and an ablation catheter is slidably tracked over the guidewire, using the guidewire lumen of the catheter. The catheter is advanced into the left atrium. While maneuvering the catheter in the heart, its position is preferably monitored by the location and mapping system disclosed in the above-noted U.S. Pat. No. 5,840,025, or alternatively by conventional imaging modalities. The anchoring balloon of the catheter is deflated during the positioning maneuver. The tip of the catheter is located at the ostium of a pulmonary vein, such that a first segment of the catheter's anchoring balloon, which is substantially the balloon's proximal third, is disposed in the left atrium, and a second segment of the anchoring balloon, composed of its remaining distal portion, lies within the lumen of the pulmonary vein.

Figure 5:
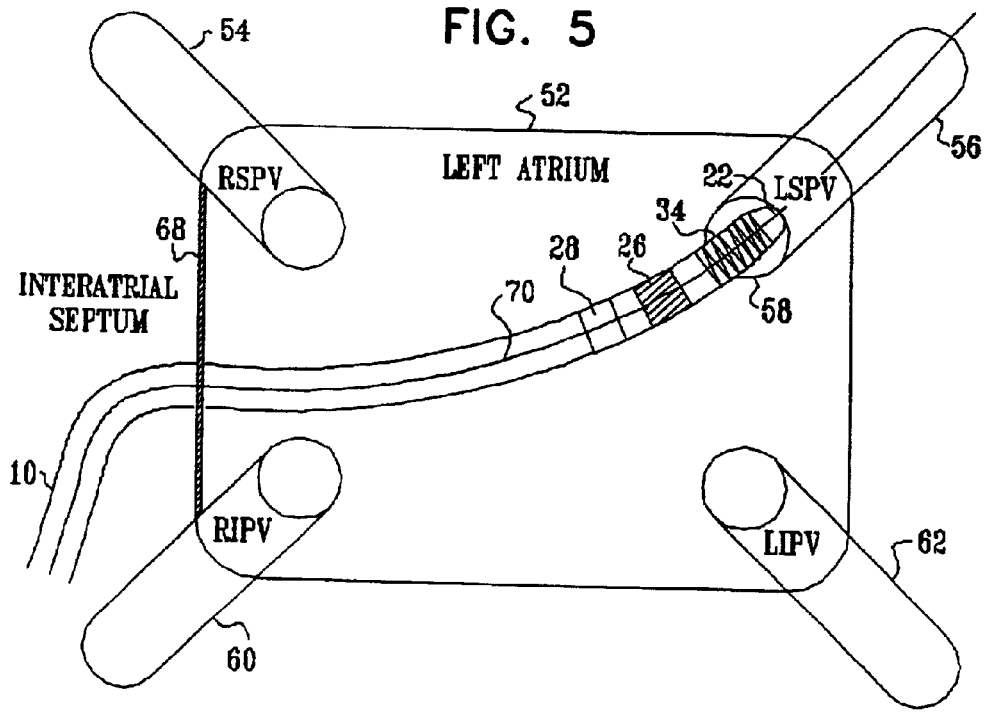
FIG. 5 schematically illustrates certain aspects of a method of intracardiac catheter access during a second phase of the method shown in FIG. 3.

Reference is now made to FIG. 5, which schematically illustrates certain aspects of the method of electrical pulmonary vein isolation in accordance with a preferred embodiment of the invention. The description of FIG. 5 should be read in conjunction with FIGS. 3 and 4. FIG. 5 represents the status at the completion of step 72 (FIG. 3). Structures in FIG. 5 that are identical to corresponding structures in FIG. 4 have been given like reference numerals. The shaft of the catheter 10 extends through the interatrial septum 68. The anchoring balloon 22 and the coil 34 lie across the ostium 58 of the left superior pulmonary vein 56, and the principal axis of the coil 34 is substantially coaxial with the left superior pulmonary vein 56. During placement, the anchoring balloon 22 is deflated, and the coil 34 is radially collapsed about the exterior wall of the anchoring balloon 22. The diameter of the collapsed coil 34 is smaller than the diameter of the left superior pulmonary vein 56, such that the coil 34 is movable within the lumen.

Referring again to FIG. 3, at step 74, the coil 34 is caused to expand radially, and circumferentially engage a portion of the inner lining of the pulmonary vein in which the target tissue is located. This is preferably accomplished by inflating the anchoring balloon, which urges the coil radially outward toward the inner wall of the pulmonary vein. In some embodiments, the shape memory of the coil alloy can be exploited to cause the coil to expand by resistively heating the coil. The radially expanded coil engages the pulmonary vein in a continuous line that runs circumferentially about the pulmonary vein proximate its ostium, and the coil is seated in position and acts as a stent for the pulmonary vein. Perfusion of the area through one of the catheter ports may be employed during step 74 to minimize stasis of blood in the region.

In step 76, once the position of the coil is confirmed, the radiofrequency generator is energized, and radiofrequency energy is conducted from the coil to the target tissue.

Reference is now made to FIG. 6, which schematically illustrates certain aspects of the method of electrical pulmonary vein isolation in accordance with a preferred embodiment of the invention. The description of FIG. 6 should be read in conjunction with FIGS. 3 and 5, in which like reference numbers denote the same element throughout. FIG. 6 represents the status at step 76 (FIG. 3). The anchoring balloon 22 is inflated, and the coil 34 is radially expanded and now functions as a stent for the left superior pulmonary vein 56. Two contact points 78 of the coil 34 and the wall of the left superior pulmonary vein 56 are illustrated, it being understood that the contact actually occurs in a continuous circumferential line. The pitch-to-radius ratio of the coil 34 is selected such that a circumferential ablation lesion produced in the target tissue bridges the distance between two adjacent loops, for example, loops 80, 82, thus forming a continuous circumferential band, having an obliquity in its orientation that conforms to the helix angle of the coil 34.

Referring again to FIG. 3, the transfer of radiofrequency energy from the emitter to the pulmonary vein in step 76 occurs in a single, relatively short application. The radiofrequency generator 42 (FIG. 2) should produce a current of 100–300 mA in order to appropriately heat a coil to about 50 degrees C., the coil of being constructed of 0.1 mm shape memory alloy wire, and having an outer diameter of 3 cm. The energy application is controlled in response to continuous electrophysiological monitoring, an end point being reached when conduction block is confirmed across the line of ablation.

Upon completion of the ablation, in step 84 the anchoring balloon is deflated and the coil radially contracted. In some embodiments, contraction of the coil is accomplished by resistive heating, exploiting the shape memory of the coil. The tip of the catheter is withdrawn into the left atrial chamber. The guidewire is also withdrawn from the pulmonary vein.

Next, at decision step 86, a test is made to determine if more pulmonary veins remain to be electrically isolated. If the determination is affirmative, then control proceeds to step 88, where the next pulmonary vein is selected. Control then returns to step 50.

If the determination at decision step 86 is negative, then control proceeds to final step 90. The anchoring balloon is deflated, and the entire apparatus withdrawn from the patient. In embodiments in which the coil is biodegradable, the coil is separated from the anchoring balloon and left in place as a stent. The procedure thereupon terminates in either case.

Alternate Embodiments

Reference is now made to FIG. 7, which is a schematic view of a coil that is constructed and operative in accordance with an alternate embodiment of the invention. A coil 92 comprises a winding of wire, formed of a shape memory alloy. The loops are folded into a plurality of zigzag folds or bends 94, which allow the coil 92 to axially expand when heated, using its shape memory properties in order to attain a desired length. The coil can also be configured to radially expand, and can be left in situ as a stent if desired following the ablation.

The loops of the coil 92 are grouped in multiple segments, of which a segment 96 and a segment 98 are referenced. For clarity of illustration the segments 96, 98 are shown as being spaced apart. However, in practice they generally are not. The coil 92 is placed on a catheter and introduced as disclosed hereinabove. It is then heated to accomplish shape adjustment. One or more ferrite cores 100 receive radiofrequency energy from an external source (not shown). The radiofrequency transmitter is adjusted such that resultant electromagnetic fields have sufficient flux to heat the coil 92, and in embodiments having a plurality of ferrite cores, to differentially heat the segments 96, 98. An external loop antenna with a radius of 25–30 cm, having 10–20 windings, is powered by a radiofrequency power amplifier carrying 200–250 watts in order to provide enough energy to heat the coil 92.

Reference is now made to FIG. 8, which is a schematic view of a coil having a shape memory that is constructed and operative in accordance with an alternate embodiment of the invention, shown following an application of heat. This embodiment is similar to the embodiment of FIG. 7, with provision for powering individual segments of the coil. A coil 102 comprises a segment 104 and a segment 106. Three electrical leads are provided within the interior of the coil 102, which are connected to a power source (not shown). A common lead 108 is connected to the segment 104 at a junction 110. The lead 108 is connected to the segment 106 at a junction 112. A second lead 114 is connected to the segment 104 at a junction 116, and a third lead 118 is connected to the segment 106 at a junction 120. When compared to the segment 104, the segment 106 is expanded longitudinally, such that its individual loops are more spaced apart from one another than the loops of the segment 104. The diameter of the segment 106 is larger than the diameter of the segment 104. This is accomplished by passing more current through the segment 106 than through the segment 104, in order to achieve differential heating.

Figure 9:
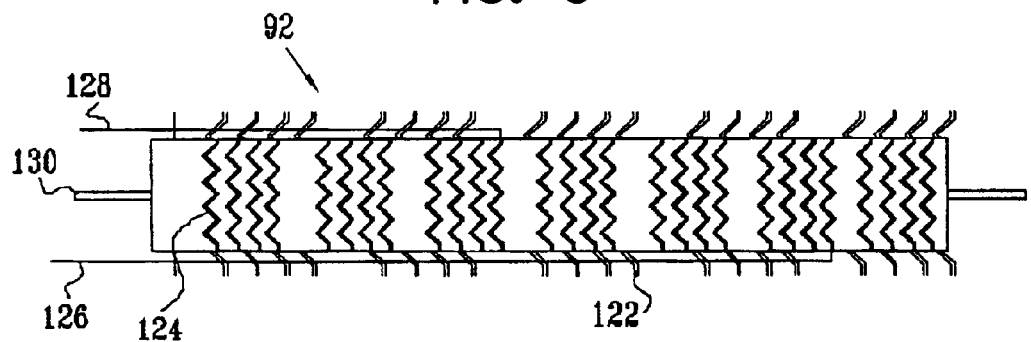
FIG. 9 is a schematic view of a coil having a shape memory that is constructed and operative in accordance with an alternate embodiment of the invention.

Reference is now made to FIG. 9, which is a schematic view of a coil having a shape memory that is constructed and operative in accordance with an alternate embodiment of the invention. It is possible to achieve differential segmental shape transformation by differentially heating of segments of a coil inductively. A coil 122 is constructed of a shape memory alloy in the same manner as the coil 92 (FIG. 7). A second coil 124, made from a conventional electrical conductor, is mounted inside the coil 122 and is connected to a power source (not shown). Passing alternating current through the coil 124 inductively heats the coil 122. Using segmental electrical leads 126, 128 and a common electrical lead 130, the power source (not shown) can produce different current flows through different segments of the coil 124 as described above. This results in correspondingly different inductive heat production in the overlying regions of the coil 122. The coil 124 is preferable mounted in the wall of the anchoring balloon 22 (FIG. 1). It is preferable that the coil 122 and the coil 124 be about the same size in order to match the electrical loads carried by each of them.

Figure 10:
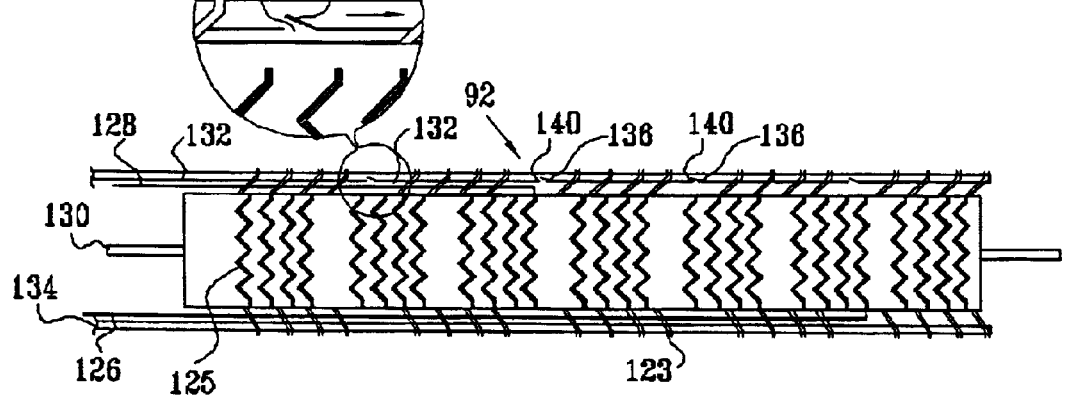
FIG. 10 is a schematic view of a coil having a shape memory that is constructed and operative in accordance with an alternate embodiment of the invention.

Reference is now made to FIG. 10, which is a schematic view of a coil 123 having a shape memory that is constructed and operative in accordance with an alternate embodiment of the invention. The embodiment shown in FIG. 10 is similar to that of FIG. 9, and like elements are given like reference numerals. A coil 125 is similar to the coil 124 (FIG. 9). However, all segments of the coil 125 are now powered by a common electrical current from a power source (not shown). Conduits 132, 134 each carry a stream of fluid, such as saline, which acts as a coolant. Control valves 136 regulate the flow through the conduits 132, 134. The saline flows out of the conduits 132, 134 through a plurality of openings 140 that are disposed opposite segments 96, 98 of the coil 123. The volume of saline effluent is locally controlled by the control valves 136, in order to achieve differential cooling of the segments 96, 98 of the coil 123. This results in regional differences in the shape transformation. A desired shape of the coil 123 can be attained by appropriately adjusting the control valves 136. It is preferable that the coil 123 and the coil 125 be about the same size in order to match the electrical loads carried by each of them.

Figure 11:
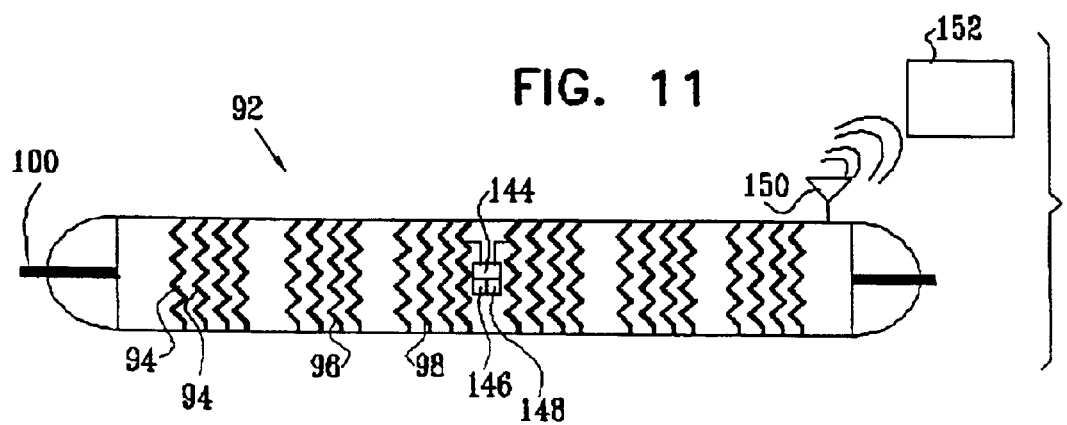
FIG. 11 is a schematic view of a coil having a shape memory that is constructed and operative in accordance with an alternate embodiment of the invention, which includes an ASIC circuit and has transmitting capability.

Reference is now made to FIG. 11, which is a schematic view of a coil having a shape memory that is constructed and operative in accordance with an alternate embodiment of the invention. The embodiment shown in FIG. 11 is similar to that of FIG. 7, and like elements are given like reference numerals. The coil 92 is now provided with an ASIC circuit 144 that includes miniature sensors 146, 148 for measuring temperature and local circuit impedance. The information obtained from the sensors 146, 148 is processed using known digital processing techniques. The coil 92 acts as an antenna, schematically referenced as antenna 150, for transmitting a signal from the ASIC circuit 144 to a control processor 152.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art which would occur to persons skilled in the art upon reading the foregoing description.

What is claimed is:

1. A method for electrically isolating a cardiac chamber, comprising the steps of:
   introducing a coil into a pulmonary vein proximate an ostium of said pulmonary vein, wherein a principal axis of said coil is substantially aligned coaxially with said pulmonary vein;
   circumferentially engaging said coil with an inner wall of said pulmonary vein by axially expanding said coil by differentially heating segments of said coil to define a circumferential region of contact between said coil and said pulmonary vein; and
   while maintaining said circumferential region of contact, conducting radiofrequency energy from said coil to said circumferential region of contact to ablate tissue in an ablation region of said pulmonary vein.

2. The method according to claim 1, wherein said step of circumferentially engaging said coil is also performed by radially expanding said coil.

3. The method according to claim 2, wherein said coil is constructed of a shape memory alloy.

4. The method according to claim 3, further comprising varying a temperature of said coil to alter a configuration thereof.

5. The method according to claim 4, wherein while performing said step of varying said temperature, said coil radially expands responsive to a shape memory thereof.

6. The method according to claim 2, wherein a proximal segment of said coil is more radially expanded than a distal segment thereof.

7. The method according to claim 6, wherein said step of radially expanding comprises tapering said coil.

8. The method according to claim 1, wherein said step of differentially heating is performed by passing different amounts of current through different ones of said segments of said coil.

9. The method according to claim 1, wherein said step of differentially heating is performed by inductive heating.

10. The method according to claim 1, wherein said step of differentially heating is performed by the steps of:
  subjecting said coil to a single electromagnetic influence for heating thereof; and
  conducting a coolant to selected ones of said segments of said coil.

11. The method according to claim 1, wherein a width dimension of said ablation region is at least as large as a pitch of said coil.

12. The method according to claim 1, wherein said step of introducing comprises the steps of:
  transferring said coil into a heart through an interatrial septum thereof; and
  while transferring said coil through said interatrial septum, conducting radiofrequency energy a second time from said coil into said interatrial septum to ablate tissue of said interatrial septum.

13. The method according to claim 12, wherein said step of conducting radiofrequency energy said second time is performed until a sufficient amount of said tissue of said interatrial septum has been ablated to accommodate a passage of said coil therethrough.

14. The method according to claim 1, wherein said coil is constructed of a biodegradable material.

15. The method according to claim 1, wherein said step of conducting radio frequency energy is performed in a single continuous application.

16. The method according to claim 1, wherein said step of circumferentially engaging said coil is performed by the steps of:
  disposing said coil about an anchoring balloon; and
  inflating said anchoring balloon to radially expand said coil.

17. The method according to claim 16, wherein following performance of said step of inflating said anchoring balloon, a proximal segment of said anchoring balloon has a larger diameter than a distal segment thereof.

18. The method according to claim 17, wherein said anchoring balloon is bilobate.

19. The method according to claim 17, wherein said anchoring balloon is pyriform.

20. A method for ablating tissue, comprising the steps of:
  providing a coil that is constructed of a shape memory material;
  introducing said coil into a hollow viscus;
  circumferentially engaging said coil with an inner wall of said viscus by axially expanding said coil by differentially heating segments of said coil to define a circumferential region of contact between said coil and said inner wall; and
  while maintaining said circumferential region of contact, conducting radiofrequency energy from said coil to said circumferential region of contact to ablate tissue therein.

21. The method according to claim 20, wherein said step of circumferentially engaging said coil is also performed by radially expanding said coil.

22. The method according to claim 21, wherein said coil is constructed of a shape memory alloy.

23. The method according to claim 21, wherein said step of providing said coil includes forming zigzag folds in a plurality of windings thereof.

24. The method according to claim 21, wherein a proximal segment of said coil is more radially expanded than a distal segment thereof.

25. The method according to claim 24, further comprising varying a temperature of said coil to alter a configuration thereof.

26. The method according to claim 25, wherein while performing said step of varying said temperature, said coil radially expands responsive to a shape memory thereof.

27. The method according to claim 24, wherein said step of radially expanding comprises tapering said coil.

28. The method according to claim 20, wherein said step of differentially heating is performed by passing different amounts of current through different ones of said segments of said coil.

29. The method according to claim 20, wherein said step of differentially heating is performed by inductive heating.

30. The method according to claim 20, wherein said step of differentially heating is performed by the steps of:
  subjecting said coil to a single electromagnetic influence for heating thereof; and
  conducting a coolant to selected ones of said segments of said coil.

31. The method according to claim 20, wherein said coil is constructed of a biodegradable material.

32. The method according to claim 20, wherein said step of conducting radiofrequency energy is performed in a single continuous application.

33. The method according to claim 20, wherein said step of circumferentially engaging said coil is performed by the steps of:
  disposing said coil about an anchoring balloon; and
  inflating said anchoring balloon to radially expand said coil.

34. The method according to claim 33, wherein following performance of said step of inflating said anchoring balloon, a proximal segment of said anchoring balloon has a larger diameter than a distal segment thereof.

35. The method according to claim 34, wherein said anchoring balloon is bilobate.

36. The method according to claim 34, wherein said anchoring balloon is pyriform.

* * * * *